(12) United States Patent
Hoffman et al.

(10) Patent No.: US 9,889,288 B2
(45) Date of Patent: Feb. 13, 2018

(54) TUBING CONNECTORS

(71) Applicant: MEDRAD, INC., Indianola, PA (US)

(72) Inventors: Raymond C. Hoffman, Gibsonia, PA (US); Martin J. Uram, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 811 days.

(21) Appl. No.: 13/831,036

(22) Filed: Mar. 14, 2013

(65) Prior Publication Data

US 2013/0331801 A1 Dec. 12, 2013

Related U.S. Application Data

(60) Provisional application No. 61/656,743, filed on Jun. 7, 2012.

(51) Int. Cl.
*A61M 39/12* (2006.01)
*A61M 39/10* (2006.01)
*F16L 37/113* (2006.01)

(52) U.S. Cl.
CPC ..... *A61M 39/12* (2013.01); *A61M 2039/1033* (2013.01); *A61M 2039/1077* (2013.01); *F16L 37/113* (2013.01)

(58) Field of Classification Search
CPC .............. A61M 39/1011; A61M 39/12; A61M 2039/1033; A61M 2039/1072; A61M 39/162; A61M 2039/1077; F16L 37/113
See application file for complete search history.

(56) References Cited

U.S. PATENT DOCUMENTS

| 2,019,402 | A | | 10/1935 | Duffy |
| 2,201,108 | A | | 5/1940 | Mahler et al. |
| 2,725,058 | A | | 11/1955 | Rathkey |
| 2,761,717 | A | | 9/1956 | Mahlke |
| 3,064,648 | A | | 11/1962 | Bujan |
| 3,193,615 | A | * | 7/1965 | Burrows ................. H01T 13/06 174/138 F |
| 3,308,979 | A | | 3/1967 | Hailes |
| 3,470,929 | A | | 10/1969 | Thornton |
| 3,584,625 | A | | 6/1971 | Swick |
| 3,596,939 | A | * | 8/1971 | Gibson ................. F16L 13/161 285/133.21 |

(Continued)

FOREIGN PATENT DOCUMENTS

DE 4438361 C1 2/1996
EP 0309426 3/1989

(Continued)

OTHER PUBLICATIONS

BPL Series Brouchure, Value Plastics, Inc. www.valueplastics.com.

(Continued)

*Primary Examiner* — Nathan R Price
*Assistant Examiner* — Justin L Zamory
(74) *Attorney, Agent, or Firm* — Joseph L. Kent; David Schramm; James R. Stevenson

(57) ABSTRACT

Sealing connectors for use in connecting tubing to tubing, tubing to needles or other implements, syringe to tubing, or syringe to needles or other implements that provide reduced turbulence and sharp transitions are described herein.

25 Claims, 11 Drawing Sheets

(56) References Cited

U.S. PATENT DOCUMENTS

| | | | |
|---|---|---|---|
| 3,718,138 A | 2/1973 | Alexandrov et al. |
| 3,790,804 A | 2/1974 | Hunt |
| 3,876,319 A | 4/1975 | Meyer |
| 3,885,560 A | 5/1975 | Baldwin |
| 3,973,554 A | 8/1976 | Tipton |
| 3,984,695 A | 10/1976 | Collica et al. |
| 4,092,546 A | 5/1978 | Larrabee |
| 4,161,178 A | 7/1979 | Genese |
| 4,307,713 A | 12/1981 | Galkin et al. |
| 4,342,337 A | 8/1982 | Underwood |
| 4,344,435 A | 8/1982 | Aubin |
| 4,372,336 A | 2/1983 | Cornell et al. |
| 4,401,108 A | 8/1983 | Galkin et al. |
| 4,409,966 A | 10/1983 | Lambrecht et al. |
| 4,472,403 A | 9/1984 | Trijzelaar et al. |
| 4,562,829 A | 1/1986 | Bergner |
| 4,585,009 A | 4/1986 | Barker et al. |
| 4,798,404 A | 1/1989 | Lyanicki |
| 4,834,708 A | 5/1989 | Pillari |
| 4,883,459 A | 11/1989 | Calderon |
| 4,902,282 A | 2/1990 | Bellotti et al. |
| 4,911,697 A | 3/1990 | Kerwin |
| 4,968,305 A | 11/1990 | Takahashi et al. |
| 4,969,176 A | 11/1990 | Marinus |
| 4,994,012 A | 2/1991 | Nakayama et al. |
| RE33,585 E | 5/1991 | Haber et al. |
| 5,105,844 A | 4/1992 | King, Sr. |
| 5,176,415 A | 1/1993 | Choksi |
| 5,274,239 A | 12/1993 | Lane et al. |
| 5,286,067 A | 2/1994 | Choksi |
| 5,312,377 A | 5/1994 | Dalton |
| 5,383,858 A | 1/1995 | Reilly et al. |
| 5,452,748 A | 9/1995 | Simmons et al. |
| 5,460,609 A | 10/1995 | O'Donnell |
| 5,472,403 A | 12/1995 | Cornacchia et al. |
| 5,490,680 A * | 2/1996 | Patel ............... F16J 15/062 277/608 |
| 5,503,187 A | 4/1996 | Simmons et al. |
| 5,509,911 A | 4/1996 | Cottone, Sr. et al. |
| 5,514,071 A | 5/1996 | Sielaff, Jr. et al. |
| 5,515,851 A | 5/1996 | Goldstein |
| 5,520,653 A | 5/1996 | Reilly et al. |
| 5,559,324 A | 9/1996 | Rapkin et al. |
| 5,569,181 A | 10/1996 | Heilman et al. |
| 5,573,515 A | 11/1996 | Wilson et al. |
| 5,676,406 A | 10/1997 | Simmons et al. |
| 5,739,508 A | 4/1998 | Uber, III |
| 5,800,397 A | 9/1998 | Wilson et al. |
| 5,800,400 A | 9/1998 | Hogan |
| 5,806,519 A | 9/1998 | Evans, III et al. |
| 5,810,988 A | 9/1998 | Smith, Jr. et al. |
| 5,828,073 A | 10/1998 | Zhu et al. |
| 5,840,026 A | 11/1998 | Uber, III et al. |
| 5,865,805 A | 2/1999 | Ziemba |
| 5,906,402 A | 5/1999 | Martin |
| 5,916,165 A | 6/1999 | Douchon |
| 5,918,443 A | 7/1999 | Phillips |
| 5,927,351 A | 7/1999 | Zhu et al. |
| 5,947,890 A | 9/1999 | Spencer et al. |
| 6,001,083 A | 12/1999 | Wilner |
| 6,096,011 A | 8/2000 | Trombley, III et al. |
| 6,162,198 A | 12/2000 | Coffey et al. |
| 6,267,717 B1 | 7/2001 | Stoll et al. |
| 6,283,182 B1 | 9/2001 | Fedeli |
| 6,317,623 B1 | 11/2001 | Griffiths et al. |
| 6,397,098 B1 | 5/2002 | Uber, III et al. |
| 6,425,174 B1 | 7/2002 | Reich |
| 6,440,107 B1 | 8/2002 | Trombley, III et al. |
| 6,450,936 B1 | 9/2002 | Smith, III et al. |
| 6,453,188 B1 | 9/2002 | Ardenkjaer-Larsen et al. |
| 6,471,674 B1 | 10/2002 | Emig et al. |
| 6,520,930 B2 | 2/2003 | Critchlow et al. |
| 6,522,144 B2 | 2/2003 | Boskamp |
| 6,585,684 B1 | 7/2003 | Hughett et al. |
| 6,586,758 B2 | 7/2003 | Martin |
| 6,589,158 B2 | 7/2003 | Winkler |
| 6,614,040 B1 | 9/2003 | Zens |
| 6,672,244 B1 | 1/2004 | Martin |
| 6,761,725 B1 | 7/2004 | Grayzel et al. |
| 6,767,319 B2 | 7/2004 | Reilly et al. |
| 6,773,373 B2 | 8/2004 | Henneken et al. |
| 6,773,673 B2 | 8/2004 | Layfield et al. |
| 6,939,302 B2 | 9/2005 | Griffiths et al. |
| 7,018,363 B2 | 3/2006 | Cowan et al. |
| 7,040,856 B2 | 5/2006 | Reich |
| 7,086,133 B2 | 8/2006 | Reich |
| 7,105,846 B2 | 9/2006 | Eguchi |
| 7,151,267 B2 | 12/2006 | Lemer |
| 7,204,797 B2 | 4/2007 | Reilly et al. |
| 7,326,186 B2 | 2/2008 | Trombley et al. |
| 7,351,227 B2 | 4/2008 | Lemer |
| 7,419,478 B1 | 9/2008 | Reilly et al. |
| 7,457,804 B2 | 11/2008 | Uber et al. |
| 7,537,560 B2 | 5/2009 | Powers et al. |
| 7,563,249 B2 | 7/2009 | Schriver |
| 7,611,486 B2 | 11/2009 | Jones et al. |
| 7,611,503 B2 | 11/2009 | Spohn |
| 7,694,610 B2 | 4/2010 | Flores et al. |
| 7,731,106 B2 | 6/2010 | Doner et al. |
| 7,772,565 B2 | 8/2010 | Wilson |
| 7,905,861 B2 | 3/2011 | Rhinehart et al. |
| 7,935,141 B2 | 5/2011 | Randall et al. |
| 7,975,733 B2 | 7/2011 | Horppu et al. |
| 8,147,364 B2 | 4/2012 | Shioiri et al. |
| 8,192,397 B2 | 6/2012 | Griffiths et al. |
| 8,198,599 B2 | 6/2012 | Bouton et al. |
| 8,454,561 B2 | 6/2013 | Uber, III et al. |
| 8,540,698 B2 | 9/2013 | Spohn et al. |
| 8,551,074 B2 | 10/2013 | Hoffman et al. |
| 2002/0012593 A1 | 1/2002 | Okuda |
| 2002/0014429 A1 | 2/2002 | Johnson |
| 2003/0040700 A1 | 2/2003 | Hickle et al. |
| 2003/0144647 A1 * | 7/2003 | Miyahara ............ A61M 39/162 604/523 |
| 2003/0151256 A1 | 8/2003 | Guala |
| 2003/0153865 A1 * | 8/2003 | Connell ................ A61M 39/14 604/28 |
| 2003/0222228 A1 | 12/2003 | Chen et al. |
| 2004/0015038 A1 | 1/2004 | Lemer |
| 2004/0064041 A1 | 4/2004 | Lazzaro et al. |
| 2004/0068248 A1 | 4/2004 | Mooney et al. |
| 2004/0115038 A1 | 6/2004 | Nuesser et al. |
| 2004/0210199 A1 | 10/2004 | Atterbury et al. |
| 2004/0254525 A1 | 12/2004 | Uber et al. |
| 2004/0254533 A1 | 12/2004 | Schriver et al. |
| 2004/0260143 A1 | 12/2004 | Reilly et al. |
| 2005/0085682 A1 | 4/2005 | Sasaki et al. |
| 2005/0107698 A1 | 5/2005 | Powers et al. |
| 2005/0113754 A1 | 5/2005 | Cowan et al. |
| 2005/0171487 A1 | 8/2005 | Haury et al. |
| 2005/0203329 A1 | 9/2005 | Muto et al. |
| 2005/0203330 A1 | 9/2005 | Muto et al. |
| 2005/0230575 A1 | 10/2005 | Zelenski et al. |
| 2005/0234424 A1 | 10/2005 | Besing et al. |
| 2005/0234428 A1 | 10/2005 | Spohn et al. |
| 2005/0247893 A1 | 11/2005 | Fu et al. |
| 2005/0251096 A1 | 11/2005 | Armstrong |
| 2005/0277833 A1 | 12/2005 | Williams, Jr. |
| 2006/0051531 A1 | 3/2006 | Kashiwamura |
| 2006/0086909 A1 | 4/2006 | Schaber |
| 2006/0151048 A1 | 7/2006 | Tochon-Danguy et al. |
| 2006/0293553 A1 | 12/2006 | Polsinelli et al. |
| 2007/0034537 A1 | 2/2007 | Fago et al. |
| 2007/0066937 A1 | 3/2007 | Jones et al. |
| 2007/0088262 A1 | 4/2007 | Jones et al. |
| 2007/0088272 A1 | 4/2007 | Jones et al. |
| 2007/0123829 A1 | 5/2007 | Atterbury et al. |
| 2007/0129591 A1 | 6/2007 | Yanke et al. |
| 2007/0129705 A1 | 6/2007 | Trombley, III et al. |
| 2007/0161970 A1 | 7/2007 | Spohn et al. |
| 2008/0038839 A1 | 2/2008 | Linder et al. |
| 2008/0131362 A1 | 6/2008 | Rousso et al. |
| 2008/0177126 A1 | 7/2008 | Tate et al. |
| 2008/0200747 A1 | 8/2008 | Wagner et al. |

(56) References Cited

U.S. PATENT DOCUMENTS

| | | |
|---|---|---|
| 2008/0200900 A1* | 8/2008 | Aeschlimann ..... A61M 39/1011 604/523 |
| 2008/0242915 A1 | 10/2008 | Jackson et al. |
| 2009/0131862 A1 | 5/2009 | Buck et al. |
| 2010/0063481 A1 | 3/2010 | Hoffman et al. |
| 2010/0160889 A1 | 6/2010 | Smith et al. |
| 2010/0185040 A1 | 7/2010 | Uber, III et al. |
| 2011/0021905 A1 | 1/2011 | Patrick et al. |
| 2011/0132482 A1 | 6/2011 | Honma et al. |
| 2011/0178359 A1 | 7/2011 | Hirschman et al. |
| 2011/0201867 A1 | 8/2011 | Wagner |
| 2011/0208129 A1 | 8/2011 | Bonnette et al. |
| 2011/0209764 A1 | 9/2011 | Uber et al. |
| 2011/0214781 A1 | 9/2011 | Horppu et al. |
| 2012/0013121 A1 | 1/2012 | Weckstrom |
| 2013/0331801 A1 | 12/2013 | Hoffman et al. |

FOREIGN PATENT DOCUMENTS

| | | |
|---|---|---|
| EP | 0333276 A1 | 9/1989 |
| EP | 0349745 | 1/1990 |
| EP | 0915760 B1 | 5/2002 |
| EP | 1616587 A1 | 1/2006 |
| EP | 1927996 A2 | 6/2008 |
| GB | 429365 A | 5/1935 |
| GB | 2040379 | 8/1980 |
| GB | 2299162 A | 9/1996 |
| IT | RM96A000148 | 3/1996 |
| JP | S60236079 A | 11/1985 |
| JP | 5184686 | 7/1993 |
| JP | 5272685 | 10/1993 |
| JP | 6165820 | 6/1994 |
| JP | 2000350783 A | 12/2000 |
| JP | 2002341040 A | 11/2002 |
| JP | 2003176892 | 6/2003 |
| JP | 2004290455 A | 10/2004 |
| JP | 2005024291 A | 1/2005 |
| JP | 2005283431 A | 10/2005 |
| WO | 9842393 A1 | 10/1998 |
| WO | 0137904 A2 | 5/2001 |
| WO | 2004004787 A2 | 1/2004 |
| WO | 2005049110 | 6/2005 |
| WO | 2006051531 A2 | 5/2006 |
| WO | 2006124775 A2 | 11/2006 |
| WO | 2007010534 A2 | 1/2007 |
| WO | 2008011401 A2 | 1/2008 |
| WO | 2008083313 A2 | 7/2008 |
| WO | 2009014367 A2 | 1/2009 |
| WO | 2009107930 A1 | 9/2009 |
| WO | 2009142944 A1 | 11/2009 |
| WO | 2009149367 A1 | 12/2009 |

OTHER PUBLICATIONS

SBL Series Quick Connects, Values Plastics, Inc. www.valueplastics.com.

The International Search Report and Written Opinion dated May 21, 2014 from corresponding PCT Application No. PCT/US2014/017949 filed on Feb. 24, 2014.

"European Search Report dated Mar. 2, 2016 in EP13800649".

The International Preliminary Report on Patentability and Written Opinion and International Search Report dated May 21, 2015 from corresponding PCT Application No. PCT/US2013/044038.

Counterpart Partial European Search Report EP10015627, dated Mar. 23, 2011.

European Search Report for European Application No. EP10015627, dated Jun. 16, 2011.

Feichtinger, M., et al., "Automatic and remote controlled ictal SPECT injection for seizure focus localization by use of a commercial contrast agent application pump," Epilepsia, vol. 48, Issue 7, pp. 1409-1413 (Jul. 2007).

International Preliminary Report on Patentability for Application No. PCT/US2013/044021, dated Jun. 6, 2014, 9 pages.

International Preliminary Report on Patentability for Application No. PCT/US2013/048484, dated Dec. 31, 2014, 6 pages.

International Search Report and Written Opinion for Application No. PCT/US2013/044021, dated Nov. 5, 2013, 10 pages.

International Search Report and Written Opinion for Application No. PCT/US2013/048484, dated Oct. 22, 2013, 8 pages.

International Search Report from counterpart PCT Application No. PCT/US2009/046437 dated Aug. 11, 2009.

Lee, J. J., et al., "Ictal SPECT using an Attachable Automated Injector: Clinical Usefulness in the Prediction of Ictal Onset Zone," Acta Radiological, vol. 50, Issue 10, pp. 1160-1168 (Dec. 2009).

The Extended European Search Report dated Jun. 11, 2014 from corresponding EP Application No. EP09759525.

"Supplementary European Search Report dated Jan. 19, 2016 from EP13809067".

* cited by examiner

TUBING CONNECTORS

CROSS-REFERENCE TO RELATED APPLICATIONS

This application claims priority from U.S. Provisional No. 61/656,743 entitled "Radiopharmaceutical Delivery System and Tube Management System" filed Jun. 7, 2012, the entirety of which is incorporated by reference herein.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Cellular therapy for the treatment of disease is expanding rapidly. There are many types of cells being used to treat an equally diverse set of diseases, and both types of cells and disease conditions are expanding rapidly. Xenogeneic cell therapies involve implantation of cells from one species into another. Allogeneic cell therapies involve implantation from one individual of a species into another individual of the same species. Autologous cell therapies involve implantation of cells from one individual into the same individual. Cell components can also have a beneficial effect on the body in selected instances. Any of the above therapies are examples of approaches that can be delivered with the systems and methods of this invention.

Deleterious effects of cellular fluid mechanics are not well addressed in many current fluid paths. For example, standard luer connectors are used almost universally in the current medical practice, including in fluid paths for cell delivery. FIGS. 1A and 1B show a standard Luer connector 10. As illustrated in FIG. 1A, standard Luer connectors 10 include a male connector 101 having a tapered extension 103 and female connectors 102 that include a tapered bore 104. These tapered sections meet when the male 101 and female 102 are mated (FIG. 1B). FIG. 1C shows an enlargement of these tapered sections during mating. The tapered extension 103 of the male connector 101 is not, typically, designed to contact the distal most part of the tapered bore 104 of the female connector 102 leaving a dead space or gap A. In addition, a first sharp transition B in the fluid path is created at the end of the male connector 101 and a second sharp transition C between the distal most part of the tapered bore 104 of the female connector 102 and the tube 106 of the female connector 102.

As fluid moves between the male connector 101 and the female connector 102 turbulence and increased shear stress is created which can result in cell damage or cell death when cells are being transported through the Luer connector 10. Moreover, a portion of the fluid transported through the connector is lost in the gap. Because certain medical procedures require delivery of relatively small volumes of fluids, such as contrast delivery, the fluid lost in the connector can have a significant effect on treatment, and in some medical procedures, this trapped material in a connector can present a biohazard.

SUMMARY OF THE INVENTION

Various embodiments are directed to a sealing connector including a first component including a distal extension having a generally cylindrical shape and a distal bore providing a cylindrical cavity at the distal end of the distal extension, a proximal cylindrical body coupled to the distal extension, the cylindrical body having a diameter at least larger than the distal extension, a central bore traversing the proximal cylindrical body and the distal extension, and a tubing section or conduit disposed within the central bore; and a second component including a generally cylindrical body and a central bore within the cylindrical body, the central bore providing a cavity sized to accommodate the distal extension of the first component, a coupling platform disposed within the central bore of the second component, the coupling platform having a generally cylindrical shape and being sized to fit within the distal bore of the first component, and a sealing member disposed within a circumferential channel created between the coupling platform and an inner surface of the central bore of the cylindrical body. In some embodiments, the distal extension of the first component may include lateral extensions and an inner surface of the central bore of the second component may include grooves configured to receive the lateral extension of the distal extension.

In some embodiments, the sealing connector may further include a transition fitting, and in certain embodiments, the transition fitting may be disposed within a portion of the central bore in the distal extension. The transition fitting of such embodiments may include a bore at least equal in diameter to a bore of a tubing section or conduit coupled to the transition fitting. In certain embodiments, the transition fitting may include a bore that is about 0.5% to about 10% larger in diameter than the diameter of a bore of a tubing section or conduit coupled to the transition fitting.

In certain embodiments, the sealing member may be an o-ring. In other embodiments, the sealing member may include about 19% to about 32% compression when the first component and the second component are coupled. In some embodiments, the second component may include a gland disposed at a distal end of the circumferential channel and the sealing member is disposed within the gland, and in particular embodiments, the sealing member may include a total volume that is the about 85% to about 98% of a total volume of the gland.

In various embodiments, a receiving conduit associated with one of the first component or the second component may be positioned to receive fluid from an exit conduit associated with the other of the first component or the second component and the receiving conduit may have a diameter that is equal to or larger than the exit conduit. In some embodiments, the receiving conduit may have a diameter that is about 0.5% to about 10% larger than the exit conduit. In certain embodiments, the receiving conduit may be tapered.

Some embodiments are directed to a sealing connector including a first component including a distal extension having a generally cylindrical shape and a distal bore providing a cylindrical cavity at the distal end of the distal extension; a proximal cylindrical body coupled to the distal extension, the cylindrical body having a diameter at least larger than the distal extension; a central bore traversing the proximal cylindrical body and the distal extension; and a tubing section or conduit disposed within the central bore; and a second component including a generally cylindrical body and a central bore within the cylindrical body, the central bore providing a cavity sized to accommodate the distal extension of the first component, a needle disposed within a central body and extending through the cylindrical body, and a sealing member disposed within a circumferential channel created between the coupling platform and an inner surface of the central bore of the cylindrical body. In some embodiments, the distal extension of the first component may include lateral extensions and an inner surface of the central bore of the second component may include grooves configured to receive the lateral extension of the distal extension.

In some embodiments, the second component may further include a coupling platform disposed within the central bore of the second component, the coupling platform having a generally cylindrical shape and being sized to fit within the distal bore of the first component and the needle extending through the coupling platform. In particular embodiments, the needle may extend beyond the coupling platform and at least a portion of the needle is received by the distal bore of the distal extension.

The sealing member of various embodiments may be an o-ring, and in some embodiments, the sealing member may include about 19% to about 32% compression when the first component and the second component are coupled. In certain embodiments, the second component may include a gland disposed at a distal end of the circumferential channel and the sealing member may be disposed within the gland. In some embodiments, the sealing member may have a total volume that is the about 85% to about 98% of a total volume of the gland. In some embodiments, a receiving conduit associated with one of the first component or the second component that is positioned to receive fluid from an exit conduit associated with the other of the first component or the second component and the receiving conduit may have a diameter that is equal to or larger than the exit conduit. In particular embodiments, the receiving conduit may have a diameter that is about 0.5% to about 10% larger than the exit conduit.

DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Figure 1A:
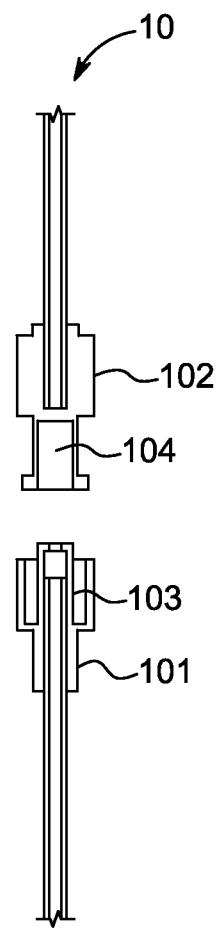
FIG. 1A-C are drawings showing a common Luer fitting.
Figure 1B:
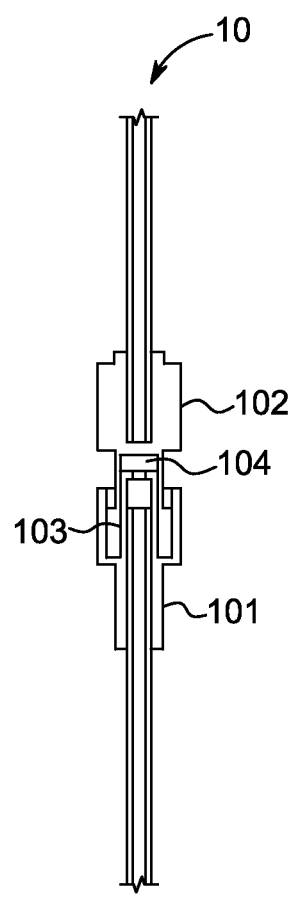
Figure 1C:
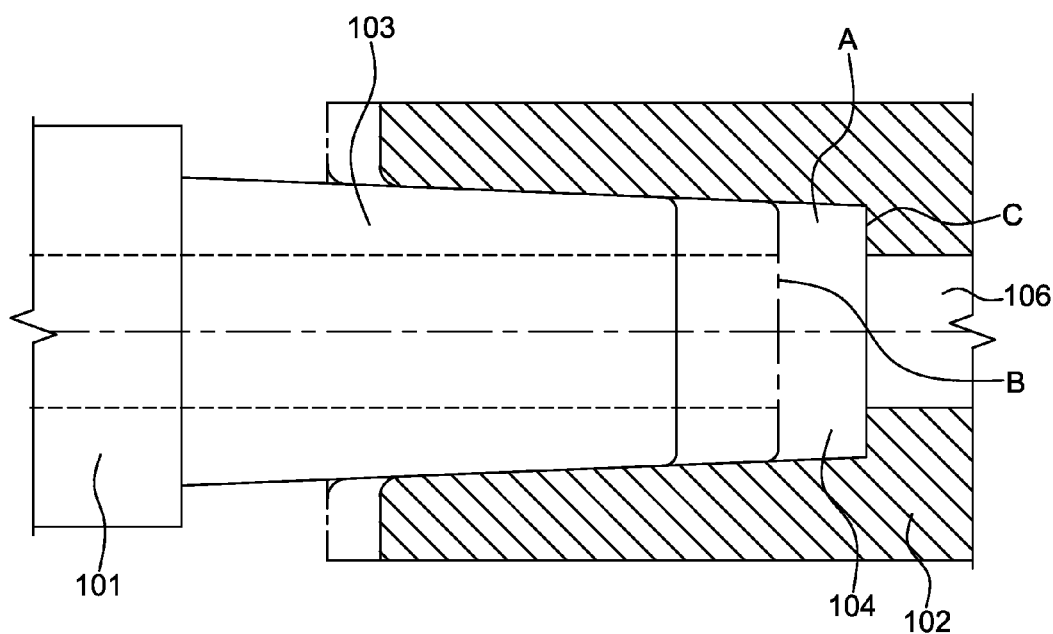

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

Embodiments described herein are directed to connectors for coupling tubing or connecting an implement such as a needle or other injection or delivery device. The connectors and implements of various embodiments provide a substantial reduction in the gap between male and female components of the connectors and reduction in sharp transitions within the connector. The turbulence, shear, and lost volume associated with standard Luer connectors is thereby eliminated.

Figure 2A:
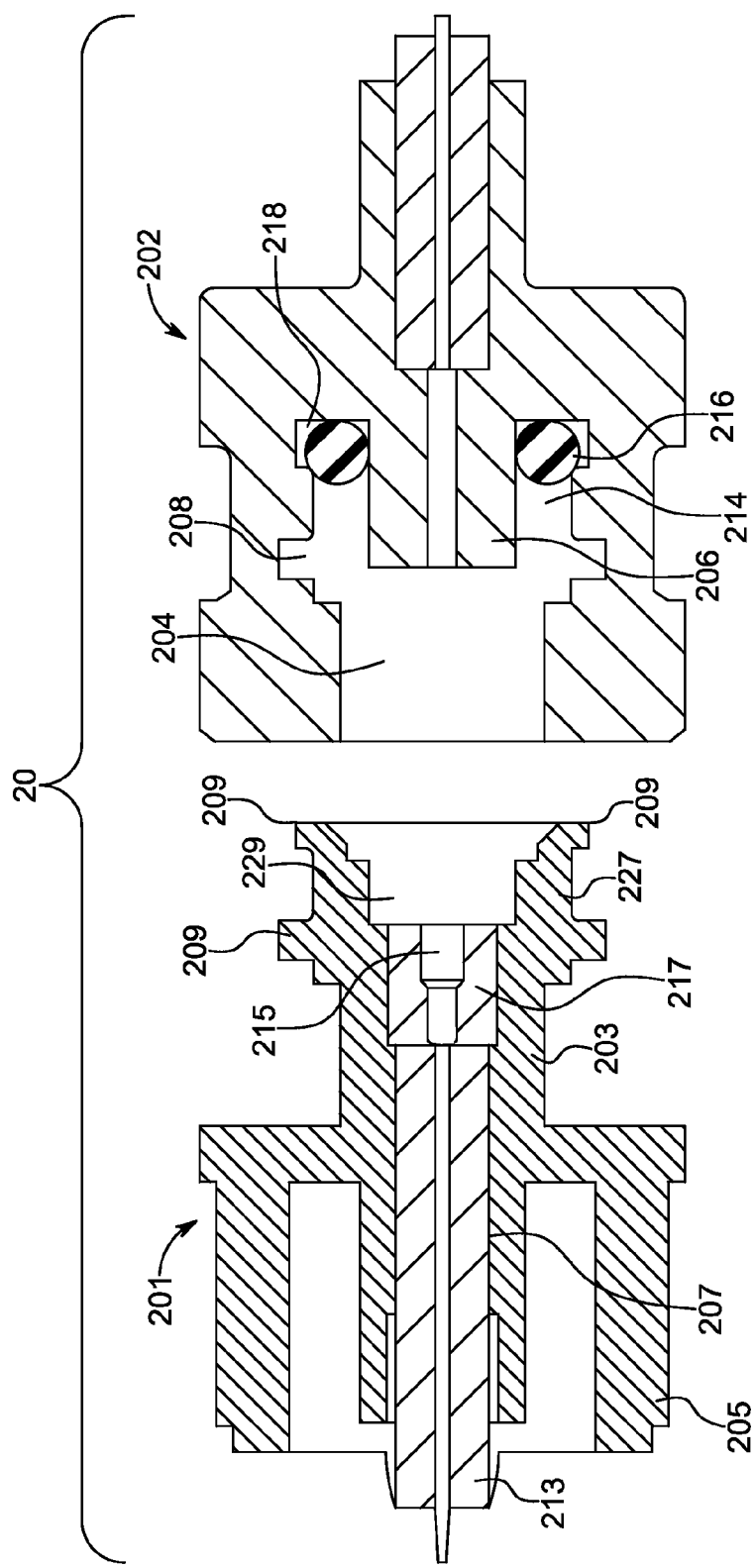
FIG. 2A-C are drawings showing the components of a sealing connector.

FIG. 2A is an illustration of an example of a connector 20 of some embodiments. Such connectors 20 include a first component 201 having a distal extension 203 and a proximal cylindrical body 205. The distal extension 203 of the first connector 201 may have a generally cylindrical shape. In some embodiments, the distal extension 203 may include a distal bore 229 providing a cylindrical cavity and creating a hollow cylindrical extension 227 on the distal end of the distal extension 203.

In some embodiments, a proximal cylindrical body 205 coupled to the proximal end of the distal extension 203. The proximal cylindrical body 205 may have a diameter that is at least greater than the diameter of the distal extension 203, and in some embodiments, the proximal distal extension may have a diameter that is substantially equal to the cylindrical body of the second component 202 as discussed below. In various embodiments, the outer surface of the proximal cylindrical body 205 may be textured to facilitate gripping and handling by a user.

The first component 201 may further include a middle bore 207 traversing the proximal cylindrical body 205 and the distal extension 203. In some embodiments, a section of tubing 213 may be disposed within the middle bore 207 to provide a pathway for fluid into or out of the first component 201. The tubing section 213 may be held within the middle bore 207 by friction, such that the tubing section 213 can be reversibly inserted and removed from the first component. In some embodiments, the tubing section 213 may be held within the central bore with an adhesive or by welding to provide a permanent connection between the tubing section 213 and the middle bore 207. In further embodiments, the first component 201 may include a conduit (not shown) disposed within the middle bore 207. The conduit in such embodiments may traverse at least a portion of the proximal cylindrical body 205, at least a portion of the distal extension 203, or both and may be designed to couple with a tubing section.

In particular embodiments, the first component 201 may include a transition fitting 217 disposed at a distal end of the middle bore 207 in the distal extension 203. The transition fitting 217 may provide a substantially flat distal surface that is aligned with the proximal surface of the distal bore 229 of the distal extension and may provide an interface for mating with the coupling platform 206 of the second component 202 (described below). In some embodiments, the transition fitting 217 may include a central channel 215 that has a diameter that is substantially equal to the diameter of a bore of the tubing section 213 or conduit, and in other embodiments, the central channel 215 may have a diameter that is larger than the diameter of a bore of the tubing section 213 or conduit. For example, the central channel 215 may have a diameter that is about 0.5% to about 10%, about 0.75% to about 5%, or about 1% to about 3% larger than the bore of the tubing section 213 or conduit.

In some embodiments, the central channel 215 of the transition fitting 217 may include steps, i.e., two or more short consecutive channels having sequentially larger bores such that the diameter of the central channel progressively increases from the proximal end near the junction with the tubing section 213 or conduit to the opening into the distal bore 229. In other embodiments, the central channel 215 may have a conical shape providing a bore having a progressively larger diameter from the junction of the tubing section 213 or conduit to the opening into the distal bore 229. Without wishing to be bound by theory, reducing the number and extent of the transitions in the central channel may reduce the occurrence of turbulence within the central channel improving fluid flow through the connector 20.

In some embodiments, the transition fitting 217 may be a separate component that is permanently attached within the middle bore 207 using an adhesive or by welding. In other embodiments, the transition fitting 217 may be molded into the first component 201. The size of the transition fitting 217 may vary among embodiments. For example, in some embodiments, as illustrated in FIGS. 2A and B the transition fitting 217 may be sized to fit within an enlargement at the distal end of the middle bore 207. In other embodiments, the transition fitting 217 may have a diameter that is substantially equal to the diameter of the middle bore 207 and may fit within the middle bore 207. In still other embodiments, a portion of the transition fitting 217 may be disposed within the middle bore 207 and another portion of the transition fitting may be disposed within the distal bore 229. In yet other embodiments, an implement such as, for example, a needle may be enclosed within a transition fitting 217. As illustrated in FIG. 2C, a portion of the transition fitting is disposed within the middle bore 207 and a portion of the transition fitting 217 is disposed within the distal bore 229 allowing the needle 240 to be held securely in place.

The transition fitting of various embodiments may be composed of any material. In some embodiments, the transition fitting may be composed of the same or a similar material as the first component. For example, in embodiments in which the first component and second component are composed of a rigid polymeric material, the transition fitting may be composed of a rigid polymeric material. Such polymeric materials are known in the art and include, but are not limited to, polyethyleneterephthalate (PET), cyclic olefin polymer, polypropylene, polystyrene, polyvinylidene chloride, polyethylene naphthalate (PEN), high-density polyethylene (HDPE), polypropylene, nylon, and the like and combinations thereof. The type of rigid polymeric material used in the transition fitting 217 may be the same or different from the rigid polymeric material used in the first component 201 and second component 202. In certain embodiments, the transition fitting 217 may be composed of an elastomeric material, and the transition fitting may be sized to create a seal when the first component 201 and the second component 202 are in communication with one another. For example, the transition fitting may be composed of an elastomeric or rubber compound such as, but not limited to, natural rubber, nitrile, neoprene, ethylene propylene, fluorocarbons, butyl rubber, polyacrylate, silicone, fluorosilicone, chromassure, thermoplastic elastomers, and the like or combinations thereof. The first component 201 and second component 202 in such embodiments may be composed of a rigid polymeric material such as those described above.

The connector 20 may further include a second component 202 having a generally cylindrical body and a central bore 204 providing a cavity sized to accommodate the distal extension 203 of the first component 201. The second component 202 may further include a coupling platform 206 extending into the cavity from the proximal end of the central bore 204. The coupling platform 206 may have a generally cylindrical shape that is sized to fit within the distal bore 229 of the first connector 201. The coupling platform 206 may be spaced from the inner walls of the central bore 204 to create a circumferential channel 214 between the lateral surface of the coupling platform 206 and the inner wall of the central bore 204.

A sealing member 216 may be disposed within the central bore 204. In some embodiments, the sealing member 216 may be disposed within a circumferential groove (not pictured) in a lateral surface of the coupling platform 206 or any inner surface of the central bore 204. In such embodiments a seal may be created when the distal bore 229 of the first component 201 receives the coupling platform 206 as the cylindrical extension 227 contacts the sealing member 216 causing it to compress into the circumferential groove. In other embodiments, as illustrated in FIGS. 2A and B, the circumferential channel 214 may terminate in a gland 218, and a sealing member 216 may be disposed within the gland 218. As discussed more thoroughly below, the sealing member 216 may be positioned to compress into the gland 218 when the first component 201 is in communication with the second component 202.

The sealing member of various embodiments may be composed of any material known in the art, and in certain embodiments, the sealing member may be composed of an elastomer or rubber such as, but not limited to, natural rubber, nitrile, neoprene, ethylene propylene, fluorocarbons, butyl rubber, polyacrylate, silicone, fluorosilicone, chromassure, thermoplastic elastomer, and the like or combinations thereof. In particular embodiments, the sealing member may be an o-ring, a ring of rectangular cross-section, or any shape suitable for a compression seal. The sealing member may be provided as a separate component that is fit into the second component after the second component has been molded. In other embodiments, the sealing member can be molded as part of the second component using, for example, overmolding or two-shot molding that provides an elastomeric sealing member on a surface of the rigid second component.

Figure 2B:
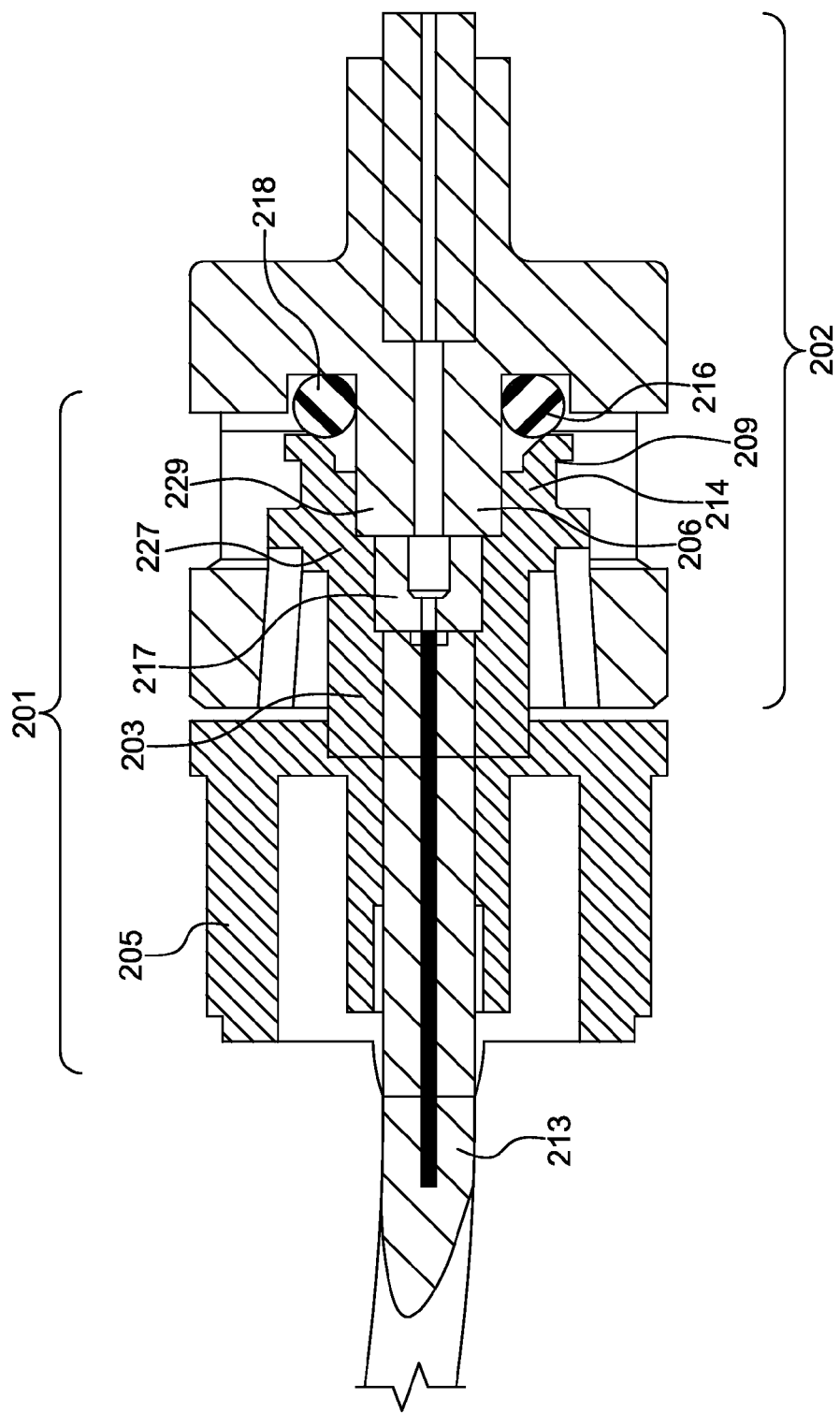
Figure 2C:
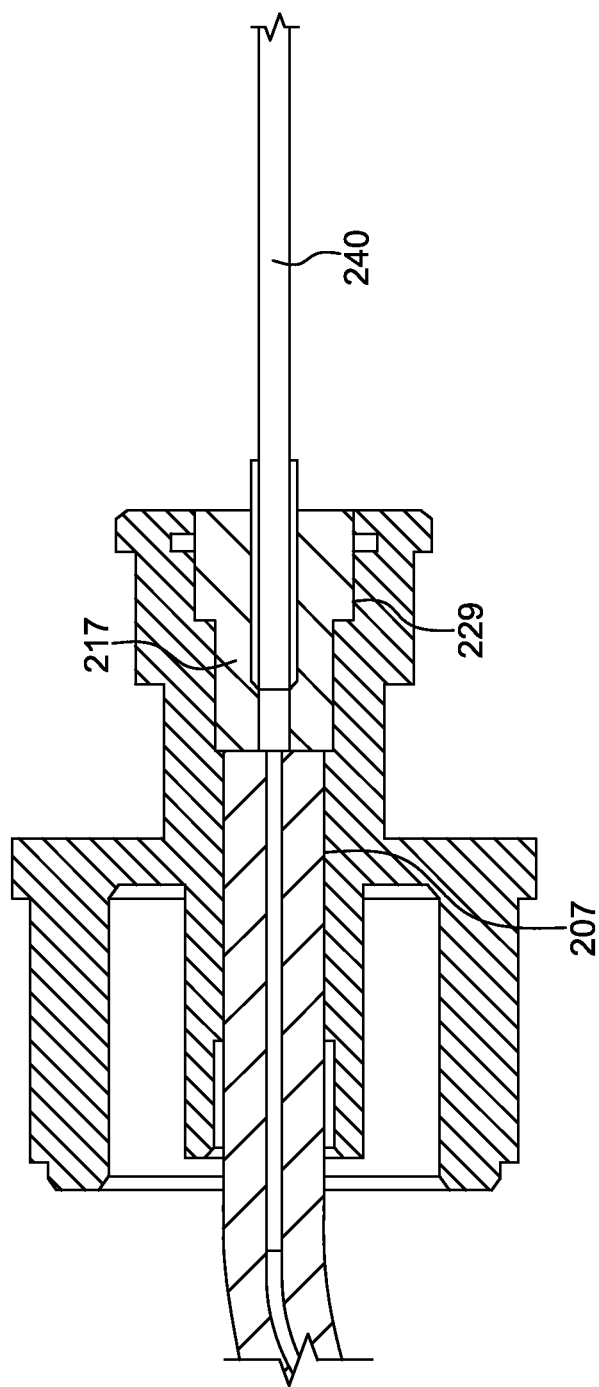

As illustrated in FIG. 2B, when the first component 201 and the second component 202 are mated, the distal extension 203 of the first component 201 may be received within the cavity created by the central bore 204 (FIG. 2A) of the second component, and the coupling platform 206 of the second component disposed in the central bore 204 may be received by the distal bore 229 (FIG. 2A) of the distal extension 203 of the first component. The cylindrical extension 227 of the first component may be received by the circumferential channel 214 of the second component and may contact the sealing member 216 causing the sealing member 216 to be pressed against the walls of the gland 218 creating a seal.

In certain embodiments, the first component 201 may include lateral extensions 209 that are sized and shaped to be received by grooves 208 in the inner walls of the central bore 204 of the second component 202. Such lateral extensions 209 and grooves 208 may be configured to provide a screw-type connection or in other embodiments, the lateral extensions 209 and grooves 208 may provide a quarter-turn type connection as illustrated in FIG. 2A and FIG. 2B. In still other embodiments, lateral extensions 209 and grooves 208 may configured to provide a compression fitting.

Figure 3:
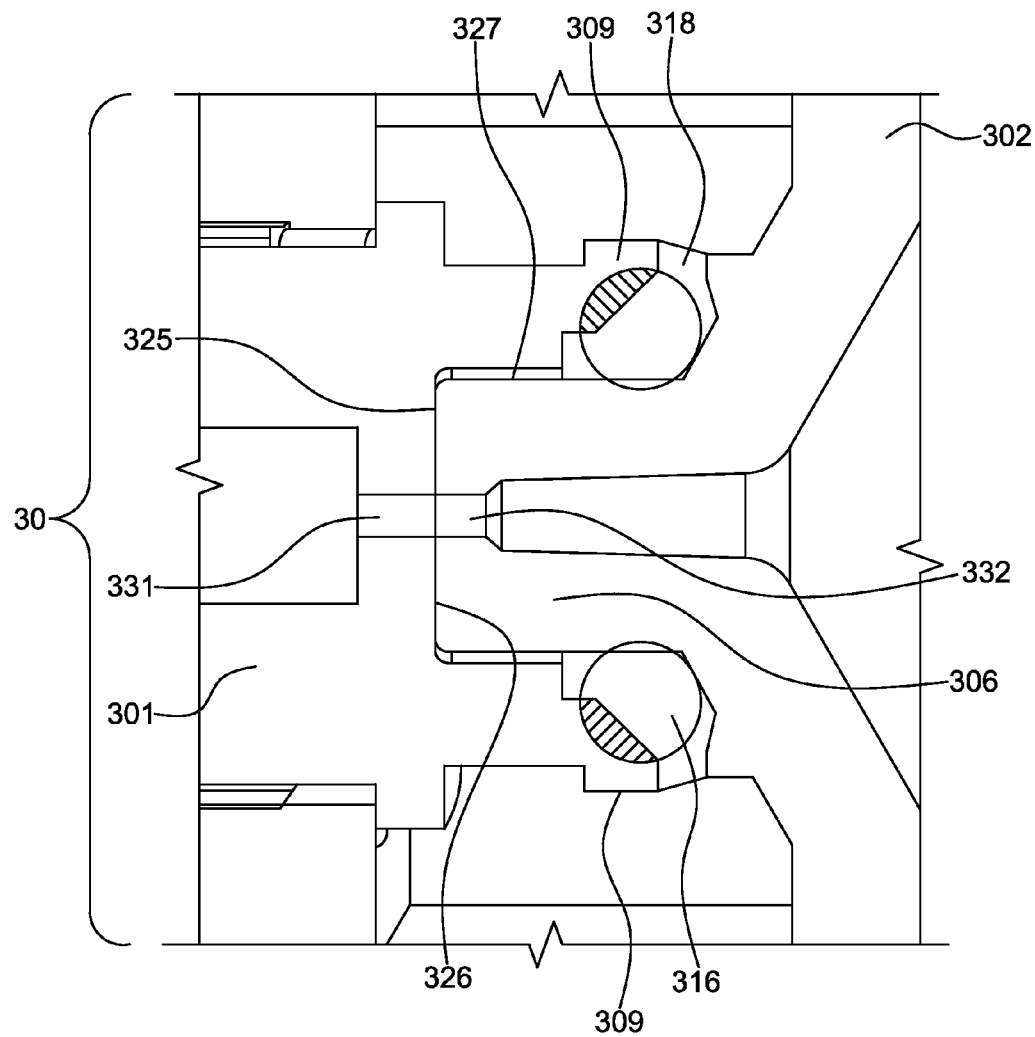
FIG. 3 is a detail drawing showing the gland and sealing member of the sealing connector.

FIG. 3 is a detailed drawing showing coupling of the first component 301 and the second component 302 at the coupling platform 306. The cylindrical extension 327 of the distal bore 229 (FIG. 2A) of the first component 301 may have a substantially uniform circumference that matches the substantially uniform outer circumference of the coupling platform 306. An upper surface 325 of the cylindrical extension 327 may be formed at about a 90° angle from the outer walls of the cylindrical extension 327 and may provide a substantially planar surface. Similarly, the upper surface 326 of the coupling platform 306 of the second component 302 may be formed at about a 90° angle from the circumferential surfaces of the coupling platform 306. A conduit or tubing section 331 extending through the first component 301 may terminate at the upper surface 325 of the cylindrical extension 327 and a conduit or tubing section 332 of the second component 302 may terminate at the upper surface 326 of the coupling platform 306.

Fluid may be transmitted from one conduit or tubing section to the other through the openings in the upper surface 326 of the coupling platform 306 of the second component 302 and the upper surface 325 of the cylindrical extension 327 of the first component 301. In some embodiments, the upper surface 325 of the cylindrical extension 327 of the first component 301 and the upper surface 326 of the coupling platform 306 of the second component 302 may contact one another to reduce a gap at the transition site, and in other embodiments, the upper surface 325 of the cylindrical extension 327 of the first component 301 and the upper surface 326 of the coupling platform 306 of the second component 302 may be separated. In embodiments in which a separation is provided between the upper surface 325 of the cylindrical extension 327 of the first component 301 and the upper surface 326 of the coupling platform 306 of the second component 302, the separation between the first component 301 and the second component 302 can be minimized during coupling to reduce leaking of fluid laterally out of the connector 30, and in certain embodiments, the upper surface 325 and the upper surface 326 of the coupling platform may butt together. In such embodiments, the circumferential channel 214 (FIGS. 2A and 2B) may be sized to allow for easy assembly of the first component 301 and second component 302 while minimizing any gap between the coupling platform 306 and the inner surfaces of the cylindrical extension 327. If this gap is too large, fluid can become trapped between the coupling platform 306 and the inner surfaces of the cylindrical extension 327 wasting the fluid.

As illustrated in FIG. 3, gland 318 and the ends of the cylindrical extension 327 can be shaped to improve the contact with the sealing member 316. For example, as illustrated in some embodiments, the distal end of the cylindrical extension 327 may be angled and at least a portion of the gland 318 may be angled to match the angle of the distal end of the cylindrical extension 327. The sealing member may be compressed between the surfaces created by these angles thereby increasing the surface area of the first component 301 and second component 302 contacting the sealing member 316. When contacted, the sealing member 316 may be compressed and portions of the sealing member 316 may expand into portions of the gland 318 to effectuate a seal. In addition, compression of the sealing member 316 may create a spring effect that pushes the first component 301 and the second component 302 away from each other. In some embodiments, this spring effect may increase the force of lateral extensions 309 of the first component 301 against lateral grooves 208 (FIG. 2A) in the second component 302 allowing the first component 301 and second component 302 to be locked in place preventing loosening or unintended disconnection.

The volume of the various components can also affect sealing. For example, in some embodiments, the sealing member may have about 19% to about 32% compression, and in other embodiments, the sealing member may have about 20% to about 30% compression or about 25% compression. The percent compression of such embodiments can be determined by dividing the volume of the portion of the sealing member that is compressed by the total volume of the sealing member. For example, the sealing member 316 of FIG. 3 may have a total volume of 42.6 mm$^3$ and 10.4 mm$^3$ of the sealing member may be compressed when the first component 301 and the second component 302 are coupled (indicated by the hashed area). The percent compression for this example is, therefore, 24%. Similarly, the volume of the gland can affect sealing. In particular, in various embodiments, about 85% to about 98% or, in some embodiments, about 90% to about 95% of the gland should be filled by the compressed sealing member during sealing. Therefore, the total volume of the sealing member 316 should be about 85% to about 98% or, in some embodiments, about 90% to about 95%, of the total volume of the gland. For example, if the gland 318 of the connector of FIG. 3 has a volume of 45.2 mm$^3$, the gland fill is 94%.

Figure 4:
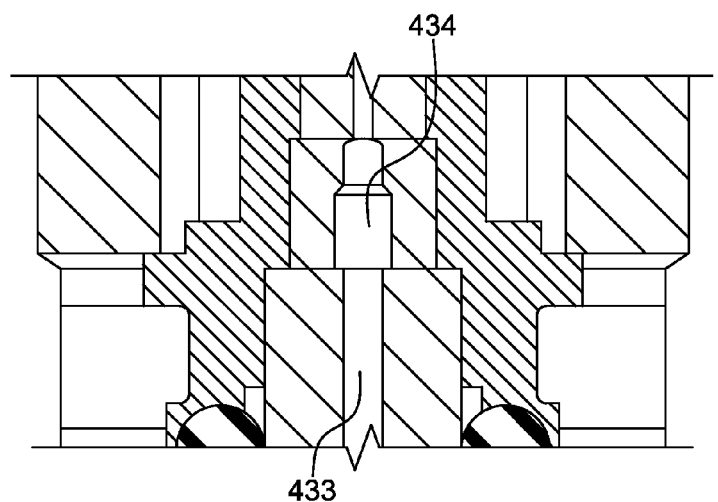
FIG. 4 is a detail drawing showing the exit conduit and receiving conduit of the sealing connector.

In some embodiments, the conduits included in the first component and the second component of the connector may be sized and shaped to improve fluid flow and reduce turbulence and shearing and the size may depend on the direction of fluid flow through the transition. For example, as illustrated in FIG. 4, in some embodiments, the exit conduit 433 may have a diameter that is equal to or smaller than the receiving conduit 434. In certain embodiments, the exit conduit 433 may be smaller in diameter than the receiving conduit 434 such that fluids are transferred from a smaller diameter exit conduit to a larger diameter receiving conduit. The diameter of the exit conduit and the diameter of the receiving conduit may vary among embodiments, and when a receiving conduit 434 is larger than an exit conduit 433, the difference in size may be relatively small to avoid creating sharp transitions. For example, in some embodiments, the diameter of the receiving conduit 434 may be about 0.5% to about 10% larger than the diameter of the exit conduit 433. In other embodiments, the diameter of the receiving conduit may be about 1% to about 7% or about 2% to about 5% larger than the diameter of the exit conduit.

While FIG. 4 suggests that the exit conduit is associated with the first component and the receiving conduit is associated with the second component, the configuration may be reversed in embodiments in which fluid flows from the second component to the first component. Thus, any connector having a larger conduit in a portion of the connector receiving fluid and a smaller conduit in the portion of the connector delivering fluid are encompassed by the invention. The receiving conduit may have a diameter that is substantially equal to exit tubing such that additional transitions are eliminated. In other embodiments, the receiving conduit may have a conical shape such that the diameter of the receiving conduit is reduced as the receiving conduit moves away from the transition between the exit conduit and the receiving conduit. Thus, a conduit having equal sizes can be used in conjunction with both the exit conduit and the receiving conduit without sharp transitions. In still other embodiments, a first transition may be provided at a junction between the exit conduit and the receiving conduit and a second transition may be provided at the junction of the receiving conduit and a tube or needle exiting the connector. The second transition may have a similar configuration as the first transition to avoid sharp transitions and turbulence. In still other embodiments, two or more transitions may be provided between the transition between the exit conduit and the receiving conduit to reduce turbulence and transition size.

Figure 5:
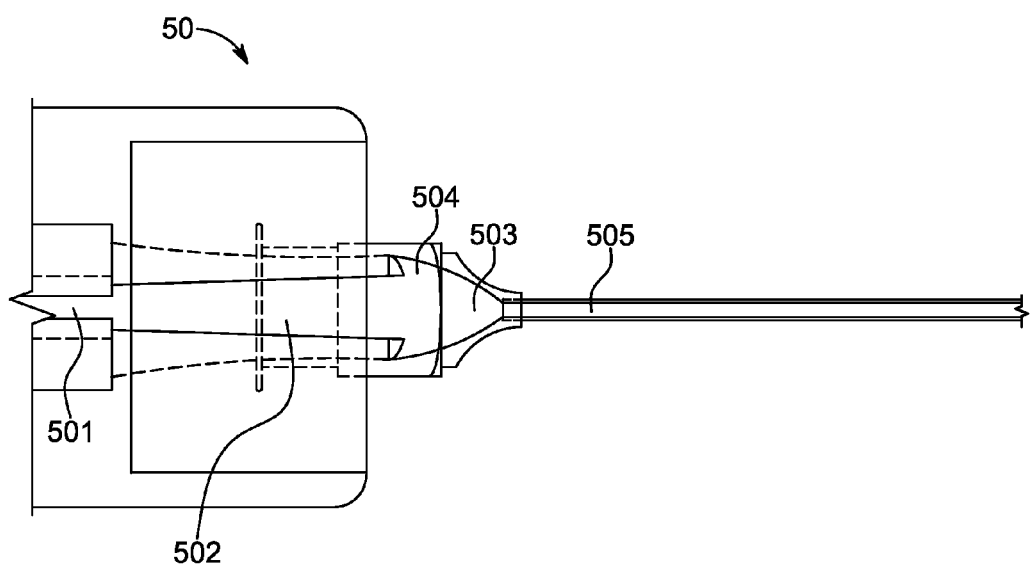
FIG. 5 is a drawing diagraming of the fluid path of a standard Luer fitting.

The difference in diameter of the exit conduit and the receiving conduit may be minimized to reduce turbulence and sharp transitions, while providing sufficient surface area for contact between the exit conduit and the receiving conduit to reduce sharp transitions created by misalignment. FIG. 5 shows a detail of the fluid path 50 created within a standard Luer connector with an outline of the components associated with the fluid path 50. In particular, FIG. 5 shows the fluid path of a section of tubing 501 which introduces fluid into a larger diameter section 502 created within the male portion of the Luer fitting. As indicated in FIG. 5, this larger diameter section 502 often has a trapezoidal cross-sectional shape with a wider diameter near the mouth of the male part of the fitting. The male part of the Luer fitting empties into a conical shaped section 503 of the fluid path created by the female part of the Luer fitting, and a transition inlet 504 is created where the male portion of the Luer fitting meets the female part of the Luer fitting. Lastly, the fluid is forced into a smaller diameter outlet section 505.

Figure 6:
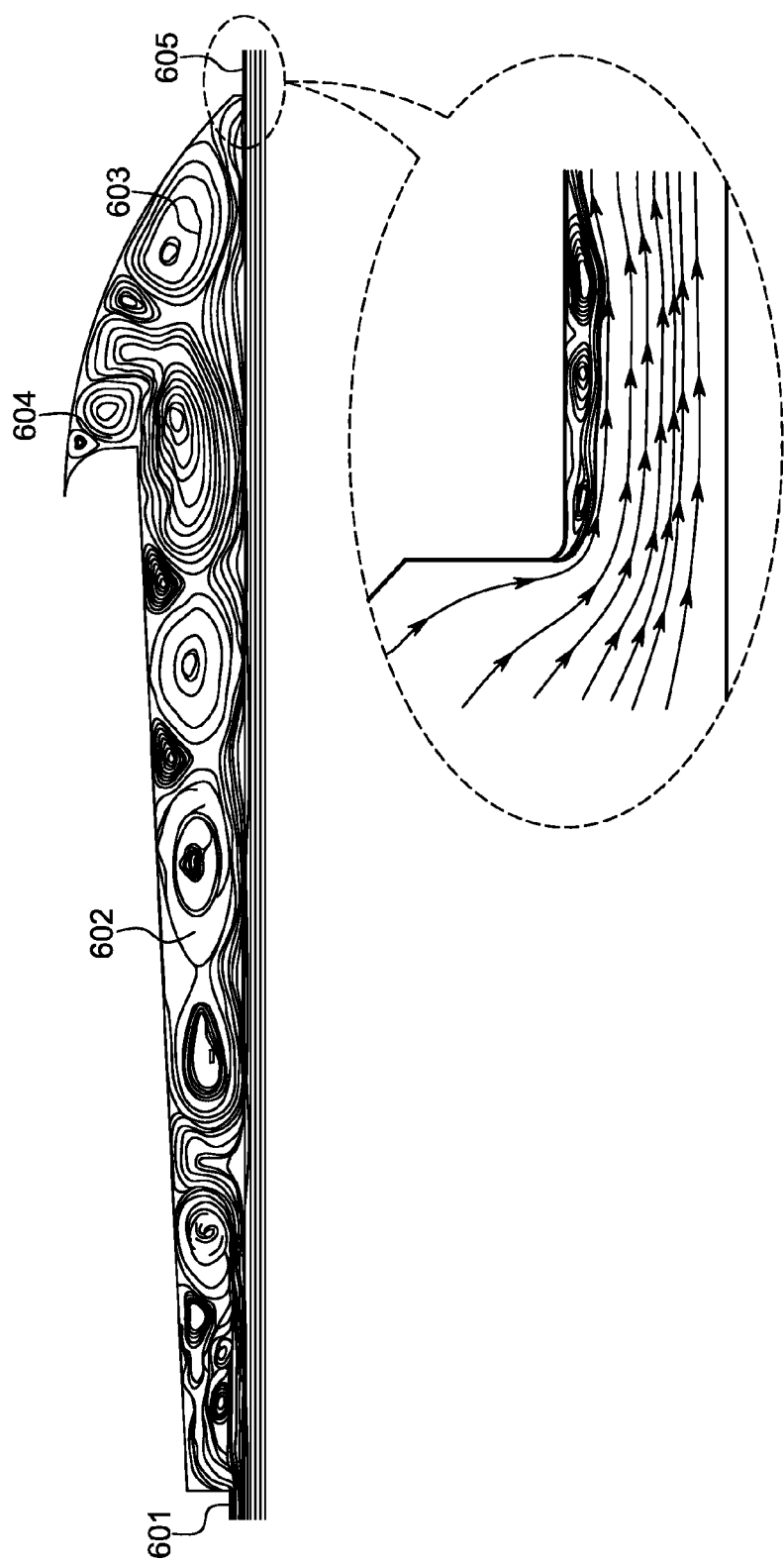
FIG. 6 is a drawing showing a fluid model of the standard Luer fitting.

FIG. 6 is a fluid model of this portion of the fluid path. As expected, various vortices are created as fluid leaves the smaller diameter tubing section 601 and enters the larger diameter section 602 created by the male part of the Luer fitting. Additional vortices are created in the conical shaped section 603 and transitional inlet 604. As indicated in the insert, further vortices are created within the outlet section 605 near the transition from the conical section 603. The changes in diameter of the various tubing sections and the vortices provide areas in the fluid path where fluid can be trapped after delivery reducing the accuracy of the amount of expelled fluid. For cell therapy uses, the larger diameter section provides places where cells can become trapped, and the vortices create turbulence that can damage the cells.

In contrast, connectors such as those described above having a transition between an exit tubing section and a receiving tubing section, in which the exit tubing section has a smaller diameter than the receiving tubing section, exhibit reduced turbulence, and the sharpness of the transition is mitigated as fluid travels into the larger diameter section. This reduction in turbulence and sharp transition reduces the potential for cell damage at the transition site. Thus, the fluid path of the connectors of embodiments shows a dramatically improved fluid path over the current standard Luer fitting depicted in FIG. 5 and FIG. 6.

Figure 7:
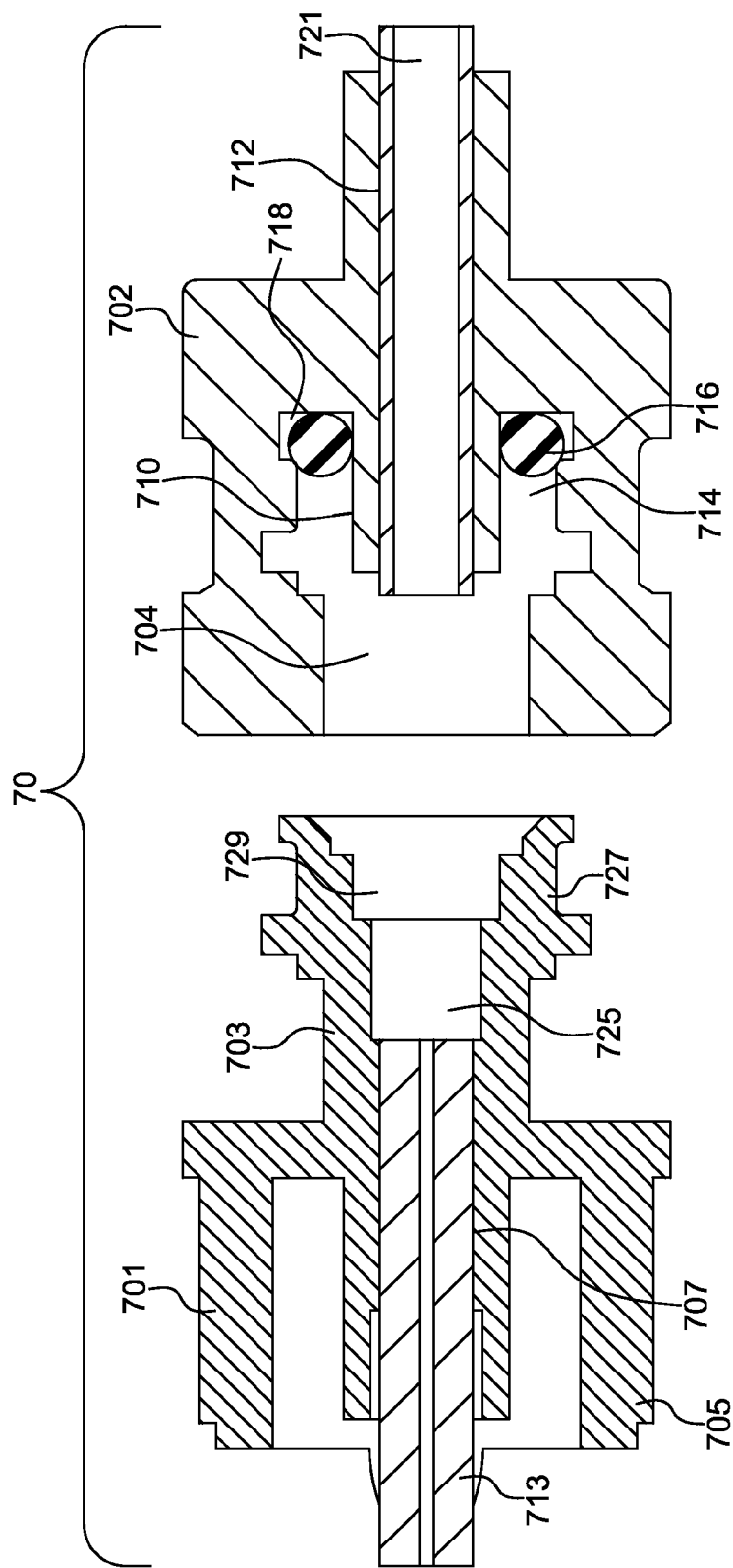
FIG. 7 is a drawing showing sealing connector associated with a needle.

The connectors of various embodiments described above can be used to connect tubing, an example of which is provided in FIG. 2A and FIG. 2B, or to connect a tube or syringe to an outlet device such as, for example, a needle. FIG. 7 shows an example of a needle designed on the principles described above. The needle connector 70 includes a first component 701 having a distal extension 703 and a proximal cylindrical portion 705. The distal extension 703 of the first connector 701 may have a generally cylindrical shape. In some embodiments, the distal extension 703 may include a distal bore 729 providing a cylindrical cavity and a hollow cylindrical extension 727 on the distal end of the distal extension 703. A tubing section 713 or conduit may be disposed within a middle bore 707. In some embodiments, the distal extension 703 may further include a needle bore 725 sized to receive a portion of a needle 721 associated with the second component 702 of the connector. The needle bore 725 may be an enlargement of the middle bore 707 as depicted in FIG. 7, or in some embodiments, the needle bore 725 may be an extension of the distal bore 729 having the same diameter of the distal bore 729.

The second component 702 may have a generally cylindrical body and a central bore 704 providing a cavity sized to accommodate the distal extension 703 of the first component 701. The second component 702 may further include a needle 721 that extends through an internal bore 712 of the second component 702 into the central bore 704. The needle 721 may be spaced from the inner walls of the central bore 704 to create a circumferential channel 714 between the longitudinal surface of the needle 721 and the inner wall of the central bore 704. In some embodiments, the circumferential channel 714 may terminate in a gland 718, and a sealing member 716 such as, for example, an o-ring, may be disposed within the gland 718. In particular embodiments, the outer surface of the needle 721 may contact the sealing member 716, and in other embodiments, the needle 721 may extend into the central bore 704 providing a coupling cylinder 710 through which the needle 721 passes. In such embodiments, at least a portion of the needle 721 may extend beyond the coupling cylinder 710 to contact the needle bore 725.

In use, the needle 721 may be received by the needle bore 725 to create a fluid connection between the first component 701 and the second component 702 minimizing the transition between the exit conduit associated with the first component 701 and the needle 721. The sealing member 716, gland 718, and other components interact in the same way as described above in relation to the tube-to-tube connector.

Figure 8:
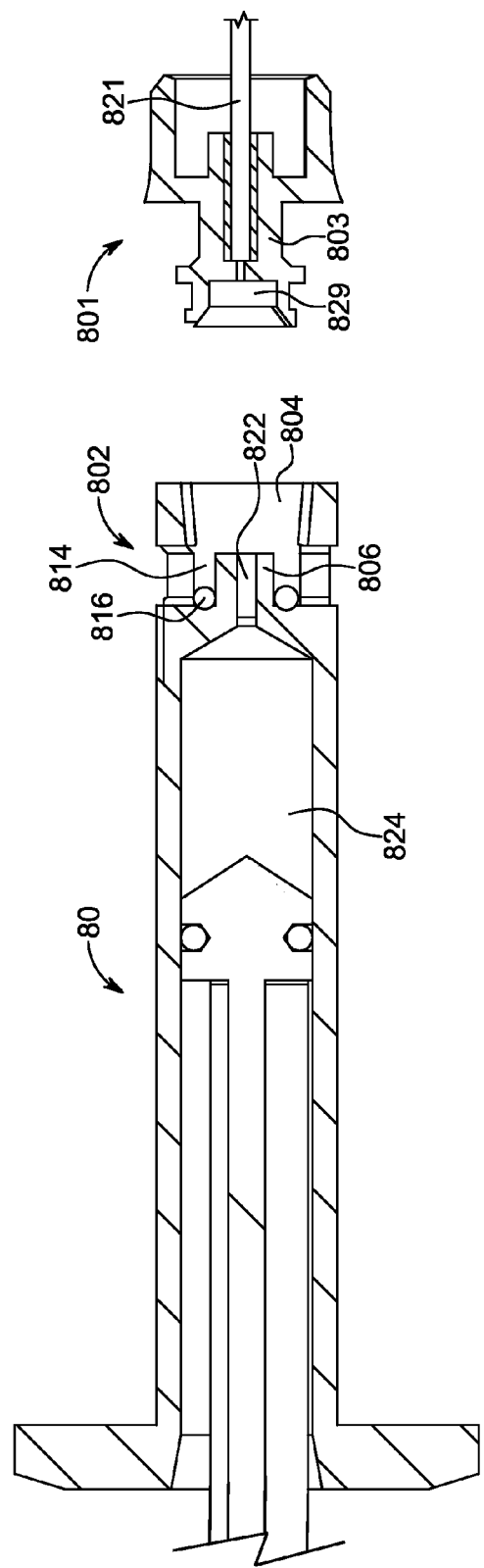
FIG. 8 is a drawing showing a syringe incorporating the sealing connectors.

Still other embodiments are directed to a syringe incorporating the connectors described above. For example, as illustrated in FIG. 8, a second connector 802 as described above may be incorporated into the distal end of a syringe 80. The first component 801 may be provided as a separate component and may include a needle 821 as illustrated or tubing section. The first component 801 may be molded into the syringe directly and may include various features described above including a generally cylindrical body and a central bore 804 providing a cavity sized to accommodate the distal extension 803 of the first component 801. The second component 802 may further include a coupling platform 806, a circumferential channel 814, and a sealing member 816. A transfer bore 822 may traverse the coupling platform 806 and connect the syringe reservoir 824 to the central bore 804.

The first component 801 of such embodiments may include a distal extension 803 having a distal bore 829 sized to receive the coupling platform 806 of the second component 802. In some embodiments, the needle 821 may terminate at the distal bore 829, and in other embodiments, a transition fitting may be provided that fluidly couples the needle 821 to the distal bore 829. As discussed above, in general, the transfer bore 822 may have a diameter that is less than or equal in diameter to the bore of the needle or the opening to a transition fitting. Thus, fluid may flow from a smaller diameter bore (transfer bore 822) to a larger diameter bore (needle bore) reducing turbulence and sharp transitions.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. A sealing connector comprising:
a first component comprising:
a distal extension having a generally cylindrical shape and a distal bore providing a cylindrical cavity at a distal end of the distal extension;
a proximal cylindrical body coupled to the distal extension, the proximal cylindrical body having an outer diameter at least larger than an outer diameter of the distal extension;
a central bore having an open proximal end and an open distal end, the central bore traversing the proximal cylindrical body and the distal extension of the first component;
a tubing section disposed within the central bore; and
a transition fitting disposed within a portion of the central bore in the distal extension of the first component, the transition fitting abutting the tubing section; and
a second component comprising:
a generally cylindrical body having a central bore defined therein, the central bore providing a cavity that accommodates the distal extension of the first component when the first component is connected to the second component;
a coupling platform disposed within the central bore of the generally cylindrical body of the second component, the coupling platform having a generally cylindrical shape and being sized to fit within the open distal end of the central bore of the first component; and
a sealing member connected to the second component and disposed within a circumferential channel between the coupling platform and an inner surface of the central bore of the generally cylindrical body of the second component such that the sealing member engages the coupling platform and the inner surface of the central bore of the generally cylindrical body,
wherein the transition fitting is interposed between the tubing section and the coupling platform and is in abutting connection with both the tubing section and the coupling platform when the first component is connected to the second component, and
wherein the sealing member is configured for minimizing a gap between the first component and the second component to prevent fluid from being trapped therebetween.

2. The sealing connector of claim 1, wherein the transition fitting defines an interface for mating the distal extension of the first component with the coupling platform of the second component.

3. The sealing connector of claim 2, wherein the transition fitting comprises a bore at least equal to or larger in diameter to a bore of the tubing section.

4. The sealing connector of claim 3, wherein the bore of the transition fitting is about 0.5% to about 10% larger in diameter than a diameter of the bore of the tubing section.

5. The sealing connector of claim 1, wherein the sealing member is an o-ring.

6. The sealing connector of claim 1, wherein the sealing member is molded into the second component.

7. The sealing connector of claim 1, wherein the sealing member is compressed by about 19% to about 32% in volume when the first component and the second component are coupled.

8. The sealing connector of claim 1, wherein the second component further comprises a gland disposed at a distal end of the circumferential channel and wherein the sealing member is disposed within the gland.

9. The sealing connector of claim 8, wherein the sealing member fills about 85% to about 98% of a total volume of the gland.

10. The sealing connector of claim 1, wherein a receiving conduit associated with one of the first component or the second component is positioned to receive fluid from an exit conduit associated with the other of the first component or the second component and the receiving conduit has a diameter that is equal to or larger than a diameter of the exit conduit.

11. The sealing connector of claim 10, wherein the diameter of the receiving conduit is about 0.5% to about 10% larger than the diameter of the exit conduit.

12. The sealing connector of claim 10, wherein the receiving conduit is tapered.

13. The sealing connector of claim 1, wherein the distal extension of the first component comprises lateral extensions and the inner surface of the central bore of the generally cylindrical body of the second component comprises grooves configured to receive the lateral extensions of the distal extension of the first component.

14. A sealing connector comprising:
a first component comprising:
   a distal extension having a generally cylindrical shape and a distal bore providing a cylindrical cavity at a distal end of the distal extension;
   a proximal cylindrical body coupled to the distal extension, the proximal cylindrical body having an outer diameter at least larger than an outer diameter of the distal extension;
   a central bore having an open proximal end and an open distal end, the central bore traversing the proximal cylindrical body and the distal extension; and
   a conduit disposed within the central bore; and
   a transition fitting disposed within a portion of the central bore in the distal extension of the first component, the transition fitting abutting the conduit; and
a second component comprising:
   a generally cylindrical body having a central bore defined therein, the central bore providing a cavity that accommodates the distal extension of the first component when the first component is connected to the second component;
   a needle disposed within an internal bore defined within and extending through the cylindrical body; and
   a sealing member connected to the second component and disposed within a circumferential channel between a longitudinal outer surface of the needle and an inner surface of the central bore of the cylindrical body,
   wherein the transition fitting is interposed between the conduit and the needle and is in abutting connection with both the conduit and the needle when the first component is connected to the second component, and
   wherein the sealing member is configured for minimizing a gap between the first component and the second component to prevent fluid from being trapped therebetween.

15. The sealing connector of claim 14, wherein the second component further comprises a coupling cylinder disposed within the central bore of the second component, the coupling cylinder having a generally cylindrical shape and being sized to fit within the distal bore of the first component and the needle extending through the coupling cylinder.

16. The sealing connector of claim 15, wherein the needle extends beyond the coupling cylinder and at least a portion of the needle is received by the distal bore of the distal extension of the first component.

17. The sealing connector of claim 14, wherein the sealing member is an o-ring.

18. The sealing connector of claim 14, wherein the sealing member is molded into the second component.

19. The sealing connector of claim 14, wherein the sealing member is compressed by about 19% to about 32% in volume when the first component and the second component are coupled.

20. The sealing connector of claim 14, wherein the second component further comprises a gland disposed at a distal end of the circumferential channel and the sealing member is disposed within the gland.

21. The sealing connector of claim 20, wherein the sealing member fills about 85% to about 98% of a total volume of the gland.

22. The sealing connector of claim 14, wherein a receiving conduit associated with one of the first component or the second component is positioned to receive fluid from an exit conduit associated with the other of the first component or the second component and the receiving conduit has a diameter that is equal to or larger than a diameter of the exit conduit.

23. The sealing connector of claim 22, wherein the diameter of the receiving conduit is about 0.5% to about 10% larger than a diameter of the exit conduit.

24. The sealing connector of claim 14, wherein the distal extension of the first component comprises lateral extensions and the inner surface of the central bore of the generally cylindrical body of the second component comprises grooves configured to receive the lateral extensions of the distal extension of the first component.

25. A sealing connector comprising:
a first component comprising:
   a distal extension having a central bore extending therethrough;
   a proximal cylindrical body coupled to the distal extension, the proximal cylindrical body having an outer diameter at least larger than an outer diameter of the distal extension;
   a conduit disposed within the central bore of the distal extension; and
   a transition fitting disposed within a portion of the central bore, the transition fitting abutting the conduit and having a central channel in fluid communication with the conduit; and
a second component comprising:
   a generally cylindrical body having a central bore defined therein, the central bore providing a cavity that accommodates the distal extension of the first component when the first component is connected to the second component;
   a coupling platform extending from the central bore of the generally cylindrical body; and
   a sealing member connected to the second component and disposed between the coupling platform and an inner surface of the central bore of the generally cylindrical body,
   wherein the transition fitting defines an interface for mating and providing an abutting connection with both the conduit in the central bore of the distal extension of the first component and the coupling platform of the second component.

* * * * *